(12) United States Patent
Úbeda Pérez et al.

(10) Patent No.: US 9,623,010 B2
(45) Date of Patent: Apr. 18, 2017

(54) ORODISPERSIBLE TABLETS

(75) Inventors: Carmen Úbeda Pérez, Cabrils-Barcelona (ES); Ignacio Díez Martín, Sant Feliu de Llobregat-Barcelona (ES); Pablo Pablo Alba, Cornella de Llobregat-Barcelona (ES)

(73) Assignee: LABORATORIOS LESVI, S.L., Barcelona (ES)

( * ) Notice: Subject to any disclaimer, the term of this patent is extended or adjusted under 35 U.S.C. 154(b) by 618 days.

(21) Appl. No.: 12/680,296

(22) PCT Filed: Sep. 30, 2008

(86) PCT No.: PCT/EP2008/063068
§ 371 (c)(1),
(2), (4) Date: Aug. 10, 2010

(87) PCT Pub. No.: WO2009/043844
PCT Pub. Date: Apr. 9, 2009

(65) Prior Publication Data
US 2010/0297031 A1 Nov. 25, 2010

Related U.S. Application Data

(60) Provisional application No. 60/977,166, filed on Oct. 3, 2007.

(30) Foreign Application Priority Data

Oct. 1, 2007 (EP) .................. 07380265

(51) Int. Cl.
| | |
|---|---|
| *A61K 31/422* | (2006.01) |
| *A61K 31/4178* | (2006.01) |
| *A61K 9/46* | (2006.01) |
| *A61P 25/20* | (2006.01) |
| *A61K 31/5513* | (2006.01) |
| *A61P 1/00* | (2006.01) |
| *A61K 31/519* | (2006.01) |
| *A61P 25/06* | (2006.01) |
| *A61P 25/24* | (2006.01) |
| *A61P 15/00* | (2006.01) |
| *A61P 29/00* | (2006.01) |
| *A61P 31/12* | (2006.01) |
| *A61K 31/4196* | (2006.01) |
| *A61K 9/00* | (2006.01) |
| *A61K 9/20* | (2006.01) |
| *A61K 31/551* | (2006.01) |

(52) U.S. Cl.
CPC ........ *A61K 31/4196* (2013.01); *A61K 9/0007* (2013.01); *A61K 9/0056* (2013.01); *A61K 9/2009* (2013.01); *A61K 9/2018* (2013.01); *A61K 9/2027* (2013.01); *A61K 9/2054* (2013.01); *A61K 9/2095* (2013.01); *A61K 31/4178* (2013.01); *A61K 31/422* (2013.01); *A61K 31/519* (2013.01); *A61K 31/551* (2013.01); *A61K 31/5513* (2013.01)

(58) Field of Classification Search
None
See application file for complete search history.

(56) References Cited

U.S. PATENT DOCUMENTS

| | | | |
|---|---|---|---|
| 6,610,266 B2 | 8/2003 | Witham et al. | |
| 2002/0071864 A1 | 6/2002 | Kim et al. | |
| 2005/0147672 A1 | 7/2005 | Ohmori et al. | |
| 2005/0244347 A1* | 11/2005 | Mehra ...................... | A61K 8/19 424/57 |
| 2006/0165781 A1 | 7/2006 | Ferran | |
| 2007/0202163 A1 | 8/2007 | Rawas-Qalaji et al. | |
| 2009/0017122 A1 | 1/2009 | Serno et al. | |
| 2010/0074948 A1* | 3/2010 | Ramtoola ............ | A61K 9/0056 424/465 |

FOREIGN PATENT DOCUMENTS

| | | |
|---|---|---|
| EP | 1488811 A1 | 12/2004 |
| EP | 1674083 A1 | 6/2006 |
| EP | 1681048 A1 | 7/2006 |
| EP | 1837019 A1 | 9/2007 |
| EP | 2213306 A1 | 8/2010 |
| JP | 2005533045 A | 11/2005 |
| WO | 03/030868 A1 | 4/2003 |

(Continued)

OTHER PUBLICATIONS

Jivraj et al., "An overview of the different excipients useful for the direct compression of tablets" PSTT (2000), vol. 3, No. 2, pp. 58-63.*

(Continued)

*Primary Examiner* — Abigail Fisher
*Assistant Examiner* — Daniel Branson
(74) *Attorney, Agent, or Firm* — Tristan A. Fuierer; Moore & Van Allen, PLLC

(57) ABSTRACT

This invention relates to a an orally disintegrating tablet obtainable by direct compression of a dry powdered mixture, said mixture comprising up to 15% by weight of calcium silicate, at least 50% of a diluent, a disintegrant agent and an active ingredient. It also relates to a process for preparing the tablets by homogeneous blending the specific excipients in powder form and subsequent direct compression of the mixture. Said tablets disintegrate quickly in the cavity of the mouth, in particular in less than 15 seconds.

14 Claims, No Drawings

(56) References Cited

FOREIGN PATENT DOCUMENTS

| WO | 03045844 A1 | 6/2003 |
| WO | 2006100875 A1 | 9/2006 |
| WO | 2007/113856 A2 | 10/2007 |

OTHER PUBLICATIONS

Forlano, Albert J., and Leonard Chavkin. "The effect of granule size upon disintegration time and capping in compressed tablets." Journal of the American Pharmaceutical Association 49.2 (1960): 67-69.*

Orally disintegrating pharmaceutical composition, IP.com Journal, IP.com, Inc., Sep. 11, 2006 (first page only).

International Search Report for PCT/EP2008/063068, Dated Apr. 1, 2009.

Makino T; Database WPI Week 200111. Derwent Publications Ltd., London, GB; XP002466620; 2001.

W.E. Ford; Textbook of Mineralogy, 4th edition; pp. 532-534, 549, 566-567 and 639-641; 1932.

\* cited by examiner

ORODISPERSIBLE TABLETS

CROSS-REFERENCE TO RELATED APPLICATIONS

This application is filed under the provisions of 35 U.S.C. §371 and claims the priority of International Patent Application No. PCT/EP2008/063068 filed on 30 Sep. 2008 entitled "Orodispersible Tablets" in the name of Carmen Úbeda Pérez, et al., which claims priority of European Patent Application No. EP07380265.4 filed on 1 Oct. 2007 and U.S. Provisional Patent Application No. 60/977,166 filed on 3 Oct. 2007, all of which are hereby incorporated by reference herein in their entirety.

FIELD OF THE INVENTION

The present invention relates to solid pharmaceutical formulations, in particular it relates to a tablet for oral administration which disintegrates rapidly by the action of saliva in the oral cavity, having also good palatability, friability, mechanical strength properties and employing a conventional manufacturing method to obtain them.

BACKGROUND OF THE INVENTION

The development of solid formulations that disintegrate quickly in the mouth without requiring water are very interesting due to the advantages that these pharmaceutical formulations provide for patients who have difficulty in swallowing, such as old people, infants, patients with mental problems and non-cooperative patients, as well as the population in general; since it makes it possible for the drug to be administered without the need for water. Moreover, since the formulation disintegrates inside the mouth, the drug may be absorbed in the oral, pharyngeal and gastrointestinal regions. The pre-gastric drug absorption avoids hepatic first-pass metabolism.

In the European Pharmacopoeia (Ph.Eur.) 5th edition, Supplement 5.2, published in June 2004, orodispersible tablets are defined as non-coated tablets for placing in the mouth which disintegrate quickly before they are swallowed. It also establishes 3 minutes as the time under which they must disintegrate in the disintegration test for tablets and capsules, according to the Ph. Eur. 2.9.1. method.

Several technologies are available to produce commercial oral fast-dissolving systems. The technologies are usually grouped according to the method employed in the preparation: freeze drying (Zydis®, Quicksoly° and Lyoc®), molding (FlashDose®) and compaction technologies.

Freeze drying (lyophilization) is a process in which a solvent is removed from a drug solution or a drug suspension containing structure-forming excipients. The tablets are characterized by a highly porous network; they quickly absorb water and dissolve, releasing the incorporated drug. The freeze drying process occurs at a low temperature, which eliminates the adverse thermal reactions that may affect drug stability. However, the freeze-drying process is very expensive and problematic when scaling up. In addition, the resulting dosage form is characterised by high friability, low stability at high temperatures and humidity levels, and by showing poor mechanical properties. Moreover, sometimes, special packaging is required.

The molding technology can be based in two different processes: the solvent method and the heat method. The solvent molding process involves preparation of a drug solution or suspension that contains a drug and the excipients and evaporating the solvent at ambient pressure and drying. In the heat molding method, the tablets are formed using a candy floss or shearform matrix, which is composed of saccharides or polysaccharides processed into amorphous floss by the simultaneous action of flash melting and centrifugal forces. The molding technology allows preparing high drug dose tablets and the resulting tablets present a rapid dissolution. However, because of their low mechanical strength, molded tablets are subject to erosion and breakage during the handling and opening of the blister pockets. Moreover, taste masking is an additional requirement with this technology.

The conventional process used to prepare fast-dissolving tablets has some advantages, such as being a well established technology, having low manufacturing cost and allowing easy technology transfer (e.g. easy to transfer to different producers). Many strategies for developing tablets with high porosity and suitable mechanical strength have been attempted, including: granulation (wet granulation, dry granulation and mold granulation) followed by compression; and direct compression.

In the granulation process, fast dissolving tablets are prepared by mixing the granules with a superdisintegrant and other appropriate excipients and compacting to obtain tablets capable of quickly disintegrating in the mouth with a limited amount of saliva. Formulation based on this technology is FlashTab® to Propragharm which is described in European patent EP 0 548 356.

On a related matter, EP1681048 describes an orally disintegrating tablet of olanzapine prepared with granulation as intermediate step and subsequent compression of the granules. A similar method is also disclosed in DE102005009241 and IP. Com. Journal, 2006, but they incorporate other active ingredients. EP1488811 refers to orally disintegrating tablets of pravastatin which are obtained by compression moulding of prepared granules. EP1674083 discloses fast disintegrating tablets prepared by first granulating a dispersion containing the ingredients in a spray-drying device, mixing the obtained granules with the active ingredient and magnesium stearate and finally, subjecting the mixture to a tabletting process.

Although tablets obtained through the granulation methodology demonstrate rapid dissolution, its rate is correlated to the hardness of the tablet and can be slower than freeze-dried tablets. Moreover, possible problems can be related to drug stability after granulation.

Direct compression represents the simplest and most cost-effective tablet-manufacturing technique from a technological point of view. Fast-dissolving tablets can be prepared by using suitable excipients with improved properties. Two known formulations based on this technology are Ziplets® to Eurand which are described in international patent application WO 99/44580 and DuraSoly® by Cima described in U.S. Pat. No. 6,024,981. Direct compression based technologies uses suitable excipients with improved properties, most notably superdisintegrants which accelerate the rate of disintegration and hence dissolution. Water soluble excipients and, sometimes, effervescent agents assist in the disintegration process. Addition of insoluble compounds which increase the efficiency of the superdisintegrant: the disintegration time decreases as the amount of hydrophilic insoluble compound increases.

Ziplets® technology is used to obtain taste masking and fast release of water-soluble or water insoluble drugs from microcapsules and granules. The resulting fast-dissolving tablets are obtained by direct compression of mixtures that contain at least one inorganic excipient that is insoluble in water, for example, calcium phosphate, one or more disintegrants, for example, crospovidone and optionally, water soluble excipients. However, the resulting compositions contain a high percentage of insoluble excipients which leave a high amount of residue in the mouth and jeopardise their palatability.

The DuraSolv® technology is designed to provide stronger tablets without packaging precautions. This technology is based on employment of conventional non-direct compression fillers (such as dextrose, mannitol, sorbitol, lactose and sucrose) in the form of fine particles that quickly dissolve without producing a gritty or sandy sensation in the mouth.

However, all the above processes for obtaining orodispersible tablets involve, to a greater or lesser extent, the following disadvantages:
  A high content of insoluble excipients or microencapsulated active ingredients that give the formula a gritty feel after they have been disintegrated in the oral cavity and, consequently, problems with palatability.
  Excessively long disintegration times in comparison with oral lyophilisates or wafers, which, in general, dissolve in less than 10 seconds.
  Insufficient mechanical resistance to resist conventional packaging and transport operations.

U.S. Pat. No. 6,610,266 describes the preparation of calcium metasilicates with low aspect ratio, and its use to prepare fast-disintegrating tablets by direct compression. However, large amounts of this excipient, about 40% by weight, are required for preparing the tablets, thus negatively affecting the size as well as the palatability of the tablet.

International application WO03/030868 also discloses the use of calcium silicate to prepare flashmelt oral dosage formulations. In this case, in addition to use even higher proportions of said excipient, the manufacturing process is more complex since it comprises a previous granulation of the ingredients.

Therefore, it is an object of this invention to provide orodispersible tablets which can be dissolved quickly in the oral cavity, which presents good palatability properties and that can be obtained by conventional processes, such as direct compression.

BRIEF SUMMARY OF THE INVENTION

The authors of the present invention have surprisingly found that a formulation based on a dry powdered mixture comprising up to 15% by weight, at least 50% by weight of a diluent and a disintegrant, allows preparing orodispersible tablets by direct compression, with disintegration times very similar to those obtained using more complex techniques. In fact, the orodispersible tablets can be disintegrated in the mouth cavity in less than 15 seconds, having also a high mechanical resistance, a low friability and higroscopicity, which involve important advantages with respect to other technologies which require preparing tablets with low resistance and high porosity in order to get short disintegration times.

Direct compression provides important advantages over other complex techniques since the active ingredient is not subjected to humidity conditions (water or other solvents) or to high temperatures, conditions which are known to diminish the stability of the oral formulation. In addition, due to its simplicity, it only requires simple machinery leading to a reduction in economic and energetic manufacturing costs.

Unlike other typical formulations used in direct compression, which are not only rather expensive but also very coarse and granular in nature resulting in a coarse dispersion in the mouth, the formulation used in the invention to prepare the orodispersable tablets provides an improved palatability. This technical feature is mainly derived from the incorporation of calcium silicate as excipient which avoids the remaining excipients to agglutinate forming agglomerates which render difficult the dispersion of the tablet in the mouth leading to an unpleasant taste and therefore to a diminished patient compliance.

Furthermore, one of the main advantages conferred by this formulation is the possibility of providing tablets with a thickness less than 30% of its major diameter, thus favouring the disintegration in the mouth and also improving the palatability. These features make even easier the administration of active ingredients to patients who have difficulty in swallowing. In addition, since the amount of calcium silicate is very low, it is also possible to elaborate tablets with a high content of active ingredient, without affecting the final size of the tablet.

Therefore, in a first aspect, the present invention relates to an orally disintegrating tablet obtainable by direct compression of a dry powdered mixture, said mixture comprising:
  up to 15% by weight of calcium silicate;
  at least 50% by weight of a diluent,
  at least a disintegrant; and
  at least an active ingredient.

Moreover, the inventors have found that by incorporating an effervescent component in the formulation, an even higher improvement in the palatability of the tablets is achieved. Consequently, the formulation of the invention can further comprise an effervescent component.

A second aspect of the present invention relates to a process for the preparation of a tablet as defined above, which comprises:
  a) mixing the dry powdered ingredients in the required amount, and
  b) applying direct compression to the mixture obtained in step a).

DETAILED DESCRIPTION OF THE INVENTION

The present invention is directed to an orally disintegrating tablet obtainable by direct compression of a dry powdered mixture, said mixture comprising up to 15% by weight of calcium silicate, at least 50% by weight of a diluent, at least a disintegrant, and at least an active ingredient. This solid formulation rapidly disintegrates in the mouth of a patient, also providing a positive organoleptic sensation since non-water soluble components are considerably minimized.

The orodispersible tablet is advantageously used in cases where administration without water is necessary, cases of administration to patients who have difficulty in swallowing tablets, or cases of administration to the elderly or to children where there is a fear of blocking the throat if it is unusual tablet form. The orodispersible tablets can be safely administered orally to humans.

Calcium Silicate

In the context of the present invention, by the term "calcium silicate" it is understood a material, natural or synthetic, of formula $CaSiO_3$ characterized by having a ratio of moles of calcium to moles of silicon, of about 1.0. In a particular embodiment, the calcium silicate used in the present invention is a naturally-occurring mineral, also known as wollastonite, having a $CaO/SiO_2$ molar ratio ranging from about 0.8 to 1.3. There exist different crystalline types of wollastonite mineral such as, type 1A (wollastonite), 2M (parawollastonite) and 7M (pseudowollastonite), being type 1A the most prevalent naturally form. These naturally-occurring calcium silicates have a crystalline form and high aspect ratios (above 3:1 and even above 20:1), that provide rigidity and strength.

Particularly preferred is the use of calcium silicate in crystalline form, more preferably ortho-, meta- and alpha-triclinic forms of calcium silicate. Examples of crystalline alpha triclinic calcium silicate are those commercially available from Aldrich Chemical, which meets the following specifications: 1.3 $m^2/g$ surface area, 0.63 g/cc bulk density, 2.90 g/cc true density and <1% w/w volatiles, and those from J. M. Huber Inc., Tomita Pharmaceutical Co., and Aldrich Chemical which meets the following specifications: 1.0 to 15 $m^2/g$ surface area, 0.50 to 0.63 g/cc bulk density, 2.40 to 2.90 g/cc true density and <1% w/w volatiles. Examples of ortho- and meta-calcium silicate forms are available from Alfa-Aesar and cover the following range of specifications for calcium silicate: 0.98 to 2.5 $m^2/g$ surface area, 0.49 to 0.90 g/cc bulk density, 2.90 to 3.30 g/cc true density and <1% w/w volatiles.

In another preferred embodiment, the calcium silicate used in the formulation is amorphous and it is generally produced synthetically. The silica source can be selected from naturally occurring pure forms of crystalline silicon dioxide or from synthetic amorphous silicon dioxide. The preferred form of silica is amorphous silicon dioxide, such as precipitated silica, silica gel, fumed silica or colloidal silica. The calcium source may be selected from the group including, silicates, oxides, carbonates, sulfates, hydroxides and salts or mixtures thereof.

Examples of amorphous calcium silicate are those commercially available from Celite Corp (micro-cel C) and J. M. Huber (Hubersorb 250NF and Hubersorb 600NF), which covers the following specifications: 190 to 210 $m^2/g$ surface area, 0.07 to 0.13 g/cc bulk density, 1.70 to 2.5 g/cc true density and 1% to 14% w/w volatiles.

In addition to the naturally-occurring or synthetic calcium silicates discussed above, it is also possible to use in the formulation synthetic calcium metasilicates as those disclosed in U.S. Pat. No. 6,610,266. Said calcium metasilicates are characterized by having a low aspect ratio and forming structured aggregates of uniform particles yielding high water absorption characteristics. Specifically, this low aspect ratio (average major axial diameter/average minor axial diameter) of the calcium metasilicate is between about 1:1 to about 2.5:1, preferably from about 1:1 to about 1.5:1, and an water absorption of from about 20 ml/100 g to about 220 ml/100 g, preferably from about 20 ml/100 g to about 100 ml/100 g. The major axis is perpendicular, although not necessarily coplanar, with the minor axis. The calcium metasilicate can be dehydrated (or "calcined").

In the context of the present invention, the term calcium silicate also includes mixtures of the different grades of the calcium silicates mentioned above.

Diluent

The formulation according to the present invention also comprises at least 50% by weight of a diluent. Examples of diluents which can be used in the invention include, without limitation, saccharides such as monosaccharides, oligosaccharides or polysaccharides, and/or their oxidised and/or reduced forms; ribose, lactose in its various forms, anhydrous, monohydrate, agglomerated forms or atomised forms; sugar alcohols such as mannitol, maltol, sorbitol, maltitol, xylitol, isomalt and erythritol, cellulose powder, microcrystalline cellulose, silified microcrystalline cellulose or derivatives of cellulose modified chemically, such as hydroxypropyl cellulose, hydroxypropyl methyl cellulose; isomalt, starch, sucrose, pharmaceutically acceptable inorganic compounds such as dibasic calcium phosphate, carbonates of calcium or of magnesium, magnesium oxide, sugar alcohols selected from mannitol, sorbitol, maltitol, maltol, isomalt, xylitol, erythritol, or mixtures thereof. In a preferred embodiment, the diluent is an oligosacharide or a sugar alcohol of medium or low solubility selected from maltol, and mannitol and mixtures thereof. More preferably, the diluent is selected from lactose, lactose monohydrate and mannitol.

Disintegrant

By the term "disintegrant" it is understood a compound which facilitates the break-up of a tablet when it is placed in aqueous environment. Disintegrants once in contact with water, swell, hydrate, change in volume or form to produce a disruptive force that opposes the efficiency of the binder/s causing the compressed table to break apart. They belong to different morphological classes and posses different functionality properties. Suitable for use in the formulation of the invention include natural starches, such as maize starch and potato starch; directly compressible starches such as starch 1500; modified or pregelatinized starches such as carboxymethylstarches and sodium starch glycolate; natural or chemically-modified cellulose, especially crosslinked sodium carboxymethyl cellulose (croscarmellose sodium) or low substituted hydroxypropyl cellulose; microcrystalline cellulose; gum, especially agar gum, and guar gum; alginic acid or salts thereof; acetates and citrates; sugars (especially lactose, mannitol and sorbitol); aluminum oxide; synthetic polymers such as cross-linked polyvinylpyrrolidones, specially crospovidone.

In a preferred embodiment of the invention, the disintegrant agent is crospovidone and croscarmellose sodium.

Active Ingredient

The active ingredient can include pharmaceutical ingredients, vitamins, minerals and dietary supplements. In a particular embodiment, the active ingredient is a pharmaceutical ingredient. Pharmaceutical ingredients that may be used include, but are not limited to, gastrointestinal function conditioning agents, anti-inflammatory agents, analgesics, agents for erectile dysfunction therapy, anti-depressants, sedatives, hypnotics, neuroleptics, anti-migraines, antihistaminic agents, for example loratadine, desloratadine, pseudoephedrine, cetirizine and mixture thereof, anti-bacterial agents, antiviral agents, cardiovascular agents, diuretics, anti-hypertensive agents anti-hypolipidemic agents, anti-ulcer agents, antiemetics, anti-asthmatic agents, anti-depressants, anti-thrombotic agents, chemotherapeutic agents, hormones, anti-helmintic agents, anti-diabetic agents, corticosteroids, peptides, proteins, recombinant drugs and mixtures thereof.

In a preferred embodiment, the pharmaceutical ingredient is selected from the group consisting of loratadine, desloratadine, aripiprazole, olanzapine, risperidone, ondansetron, zolmitriptan, rizatriptan, frovatriptan, eletriptan, almotriptan and salts thereof.

In another particular embodiment of the invention, the active ingredient is selected from a vitamin, a mineral, a dietary supplement and mixtures thereof.

As used in this disclosure, the term "vitamin" refers to trace organic substances that are required in the diet. Examples of vitamins include, without limitation, thiamine, riboflavin, nicotinic acid, pantothenic acid, pyridoxine, biotin, folic acid, vitamin $B_{12}$, lipoic acid, ascorbic acid, vitamin A, vitamin D, vitamin E and vitamin K. The term vitamin also includes choline, carnitine, and alpha, beta and gamma carotenes.

The term "mineral" refers to inorganic substances, metals, and the like required in the human diet. Examples of minerals include, without limitation, calcium, iron, zinc, selenium, copper, iodine, magnesium, phosphorous, chromium and the like, and mixtures thereof.

The term "dietary supplement" as used herein means a substance which has an appreciable nutritional effect when administered in small amounts. Dietary supplements include, without limitation, ingredients such as pollen, bran, wheat germ, kelp, cod liver oil, ginseng, fish oils, amino acids, proteins and mixtures thereof. As will be appreciate, dietary supplements may incorporate vitamins and minerals.

In general, the amount of active ingredient incorporated in the formulation may be selected according to known principles of pharmacy. An effective amount of pharmaceutical ingredient is specifically contemplated. By the term "effective amount" it is understood that the amount or quantity of a drug or pharmaceutically active substance which is sufficient to elicit the required therapeutic response. As used with reference to a vitamin or mineral, the term "effective amount" means an amount at least about 10% of the recommended daily dose.

The amount of the active ingredient used can vary greatly. Those of ordinary skill in the art will appreciate that the physical characteristics of the active ingredient, the size of the tablet and the requirements of other ingredients will directly influence its limiting content in the formulation. However, generally, the active ingredient does not exceed 30% by weight, preferably from 1 to about 20% by weight, most preferably from 1 to about 15% by weight based on the total weight of the formulation. In addition, the authors of the present invention have found that by incorporating an effervescent component in the formulation of the invention an improvement of the palatability of the tablets is obtained, thus providing a pleasant organoleptic sensation. Therefore, the formulation of the present invention can further comprise an effervescent component. Suitable effervescent components that can be used in the formulation of the invention are a mixture comprising a $CO_2$ donor and an organic acid. Typical $CO_2$ donors include carbonates and bicarbonates such as sodium bicarbonate, potassium bicarbonate, sodium carbonate and potassium carbonate. Examples of organic acids include, without limitation, citric, malic, tartaric, adipic and fumaric acid.

The pharmaceutical composition of the present invention can also include other conventional excipients like surfactants, flavouring agents, lubricants, sweeteners, glidants, antiadherants and mixtures thereof, which affect the elegancy and performancy of the orodispersible pharmaceutical compositions. The additional excipients used in said formulation are present in small amounts, e.g. generally less than 10%, preferably 5% of the total mass of the tablet.

The lubricant is used herein as an additional excipient that can affect the performance of an orodispersible pharmaceutical composition. Suitable examples of lubricants include but are not limited to talc, sodium benzoate, sodium stearyl fumarate (Pruv), calcium stearate, magnesium stearate, zinc stearate, glyceryl behenate, stearic acid and glyceryl monostearate. Preferred lubricant for the composition of the present invention is sodium stearyl fumarate or magnesium stearate or combination thereof. Preferably the lubricant(s) of the present invention are used in an amount of about 0.25 to 5% by weight.

Suitable flavouring agents used in the composition of the present invention include but are not limited to strawberry, cherry, orange, peppermint, black currant, banana, raspberry, red fruits, wild berries and caramel flavour. Preferably the flavouring agents of the present invention are used in an amount of less than 2% by weight.

The sweetener may be selected from the group especially comprising aspartame, potassium acesulfame, sodium saccharinate, neohesperidine dihydrochalcone, sucralose, sucrose, fructose, monoammonium glycyrrhizinate, and mixtures thereof. Preferably the sweetener of the present invention is used in an amount of about 1 to 2% by weight.

The orally disintegrating tablet of the invention can be rapidly disintegrated in the mouth, having also a high mechanical resistance and low friability. The term friability refers to an index which provides a measure of the ability of a tablet to withstand both shock and abrasion without crumbling the handling of manufacturing, packaging, shipping and consumer use. The orodispersible tablet of the present invention presents a friability no greater than 1%, preferably no greater than 0.8%.

The formulation used in the invention allows preparing orodispersible tablets with a very low thickness, thus increasing the tablet surface and consequently the speed of disintegration. In a particular embodiment of the invention, the orodispersible tablet has a thickness less than 30% of its major diameter. This small thickness facilitates the disintegration of the tablet as well as its palatability. Thus, in a particular embodiment, the orodispersible tablet of the invention disintegrates in less than 20 seconds, more preferably in less than 15 seconds, even more preferably in less than 10 seconds.

The orally disintegrating tablet of the present invention is prepared by direct compression of a dry powdered mixture. The term "direct compression" is used in the context of the invention to define a process by which tablets are compressed directly from powder blends of the active ingredient and the excipients (including diluents, fillers, disintegrants and lubricants), which flow uniformly into a die cavity and form a firm compact. No pretreatment of the powder blend by wet or dry granulation procedures is applied. When potent drugs are incorporated in the formulation, these can be sprayed out of solution onto one of the excipients.

By the term "dry powdered mixture" it is understood a mixture of ingredients in powder form, wherein said ingredients have been previously and independently passed through a sieve with mesh size lower than 650 μm, that guarantees a mean particle size lower than that size, without having been subjected to any granulation process, dissolution or dispersion in a liquid medium.

In a particular embodiment, the calcium silicate, the diluent, the disintegrant agent and the active ingredient are homogeneously mixed together in powder form to provide a homogeneous mixture. The mixture is then subjected to direct compression to provide a solid preparation in the form of a tablet. For example, the powder mixture is fed to the die of a tablet press and sufficient pressure is applied to form the solid tablet. Such pressure can vary, and typically ranges about 1.000-20.000 N, being particularly preferable 3.000-15.000 N. Direct compression is the easiest way of manufacturing tablets and has the great advantage of having a low manufacturing cost. Moreover, it uses conventional equipment, commonly available excipients and a limited number of process steps.

The resulting compressed solid preparation possesses a suitable strength and hardness and does not disintegrate during distribution and storage.

The following non-limiting examples will further illustrate specific embodiments of the invention. They are, however, not intended to be limiting the scope of the present invention in any way.

EXAMPLES

Example 1

Orodispersible tablets were made according to the method defined below using the formulation having the ingredients shown in table I:

TABLE I

|   | mg | % (w/w) |
|---|---|---|
| 1. Olanzapine | 10.00 mg | 12.50% |
| 2. Lactose monohydrate | 54.61 mg | 68.26% |
| 3. Hydroxypropylcellulose low-substituted | 3.20 mg | 4.00% |
| 4. Crospovidone | 2.40 mg | 3.00% |
| 5. Calcium silicate | 7.20 mg | 9.00% |
| 6. Aspartame | 1.07 mg | 1.33% |
| 7. Banana Flavor | 0.16 mg | 0.20% |
| 8. Orange Flavor | 0.16 mg | 0.20% |
| 9. Colloidal anhydrous silica | 0.40 mg | 0.50% |
| 10. Magnesium stearate | 0.80 mg | 1.00% |
| Total | 80 mg | 100% |

Manufacturing Method

The orodispersible tablet was obtained according to the following procedure:
  a) the components of the formulation were weighted;
  b) components 4 and 5 were sieved through a screen with a mesh size of 0.5-0.6 mm;
  c) the materials of stage "b" were mixed in a suitable container until a homogeneous mixture was obtained;
  d) components 1, 2, 3, 6, 7, 8 and 9 were sieved through a screen with a mesh size of 0.5-0.6 mm;
  e) the materials of stage "d" were mixed with the blend obtained in stage "c" in a suitable container until a homogeneous mixture was obtained;
  f) the component 10 was sieved through a screen with a mesh size of 0.3-0.4 mm, it was incorporated into the homogeneous mixture obtained in section "e", and the whole was mixed in a suitable container for approximately 5 minutes
  g) the mixture powder obtained in stage "f" was compressed in a tabletting machine equipped with suitable punches.

|   |   |
|---|---|
| Disintegration time | 10 sec. |
| Weight | 80 mg |
| Resistance to crushing | 33 N |
| Friability | <0.1% |
| Thickness | 1.77 mm |

Disintegration Time

The disintegration time has been measured according to the following procedure.

A filter paper was placed on the bottom of Petri dish and then purified water was poured to achieve a homogeneous humectation. The tablet prepared as defined above was placed on the humectated paper and the complete disintegrating time of the tablet was measured. The test was done six times and the results were averaged.

Tablet Weight 20 tablets were weighted in an automatic balance and the average mass was calculated.

Resistance to Crushing

The resistance to crushing of 10 tablets is determined according to the equipment and method described in the Ph. Eur. 2.9.8.

Friability

The friability of the tablets is performed according to the equipment and method described in the Ph. Eur. 2.9.7.

Thickness

The thickness of a tablet is the distance between the middle point of the two surfaces of the tablet and it is measured with a micrometer.

Example 2

The tablet was prepared according to the procedure described below using the formulation having the ingredients shown in table II:

TABLE II

|   | mg | % (w/w) |
|---|---|---|
| 1. Olanzapine | 10.00 mg | 13.33% |
| 2. Lactose monohydrate | 40.98 mg | 54.63% |
| 3. Hydroxypropylcellulose low-substituted | 3.00 mg | 4.00% |
| 4. Crospovidone | 3.00 mg | 4.00% |
| 5. Calcium silicate | 9.00 mg | 12.00% |
| 6. Aspartame | 1.00 mg | 1.33% |
| 7. Calcium carbonate | 3.00 mg | 4.00% |
| 8. Tartaric acid | 3.75 mg | 5.00% |
| 9. Banana Flavor | 0.15 mg | 0.20% |
| 10. Colloidal anhydrous silica | 0.38 mg | 0.50% |
| 11. Magnesium stearate | 0.75 mg | 1.00% |
| Total | 75 mg | 100% |

Manufacturing Method

The orodispersible table was obtained according to the following procedure:
  a) components of the formulation were weighted;
  b) components 4 and 5 were sieved through a screen with a mesh size of 0.5-0.6 mm;
  c) the materials of stage "b" were mixed in a suitable container until a homogeneous mixture has been obtained;
  d) components 1, 2, 3, 6, 7, 8, 9 and 10 were sieved through a screen with a mesh size of 0.5-0.6 mm;
  e) the materials of stage "d" were mixed with the blend obtained in stage "c" in a suitable container until a homogeneous mixture was obtained;
  f) the component 11 was sieved through a screen with a mesh size of 0.3-0.4 mm, it was incorporated into the homogeneous mixture obtained in section "e", and the whole was mixed in a suitable container for approximately 5 minutes;
  g) the mixture powder obtained in stage "f" was compressed in a tabletting machine equipped with suitable punches.

|   |   |
|---|---|
| Disintegration time | 11 sec. |
| Weight | 75 mg |
| Resistance to crushing | 36 N |
| Friability | 0.17% |
| Thickness | 1.65 mm |

Example 3

The tablet was prepared according to the procedure described below using the formulation having the ingredients shown in table III:

TABLE III

| PR-42 | mg | % (w/w) |
| --- | --- | --- |
| 1. Zolmitriptan | 2.5 | 2.77 |
| 2. Mannitol granular | 73.45 | 81.61 |
| 3. Crospovidone | 4.5 | 5 |
| 4. Calcium silicate | 6.3 | 7 |
| 5. Aspartame | 0.9 | 1 |
| 6. Orange Flavour | 0.9 | 1 |
| 7. Strawberry Flavour | 0.1 | 0.11 |
| 8. Magnesium Stearate | 1.35 | 1.5 |
| Total | 90 | 100 |

Manufacturing Method

The orodispersible table was obtained according to the following procedure:
a) the components of the formulation were weighted;
b) component 1, enough amount of 2 to achieve a homogeneous mixture, 3 and 4 were sieved through a screen with a mesh size of 0.5-0.6 mm;
c) the materials of stage "b" were then mixed together in a suitable container until a homogeneous mixture was obtained;
d) the rest of component 2, and components 5, 6, and 7 were sieved through a screen with a mesh size of 0.5-0.6 mm;
e) the materials of stage "d" were mixed together in a suitable container until a homogeneous mixture was obtained;
f) component 8 was sieved through a screen with a mesh size of 0.5-0.6 mm, it was incorporated into the homogeneous mixture obtained in section "e", and the whole was mixed in a suitable container for approximately 2 minutes;
g) the mixture powder obtained in stage "f" was compress in a tabletting machine equipped with suitable punches.

| | |
| --- | --- |
| Disintegration time | 9 sec. |
| Mean tablet weight | 90 mg |
| Tablet crushing strength | 17 N |
| Tablet friability | 0.45% |
| Tablet thickness | 2.1 mm |

Example 4

The tablet was prepared according to the procedure described below using the formulation having the ingredients shown in table IV:

TABLE IV

| | mg | % (w/w) |
| --- | --- | --- |
| 1. Ondansetron base | 4.00 mg | 5.30% |
| 2. Spry dried mannitol | 42.38 mg | 56.50% |
| 3. Microcrystalline cellulose | 11.25 mg | 15.00% |
| 4. Sodium croscarmellose | 2.25 mg | 3.00% |
| 5. Calcium silicate | 6.75 mg | 9.00% |
| 6. Aspartame | 1.00 mg | 1.30% |
| 7. Calcium carbonate | 3.39 mg | 4.52% |
| 8. Tartaric acid | 2.24 mg | 2.98% |
| 9. Peppermint flavour | 1.00 mg | 1.30% |
| 10. Magnesium stearate | 0.75 mg | 1.0% |
| Total | 75 mg | 100.00% |

Manufacturing Method

The orodispersible table was obtained according to the following procedure:
a) the components of the formulation were weighted;
b) components 4 and 5 were sieved through a screen with a mesh size of 0.5-0.6 mm;
c) the materials of stage "b" were mixed in a suitable container until a homogeneous mixture was obtained;
d) components 1, 2, 3, 6, 7, 8, 9 and 10 were sieved through a screen with a mesh size of 0.5-0.6 mm;
e) the materials of stage "d" were mixed with the blend obtained in stage "c" in a suitable container until a homogeneous mixture was obtained;
f) the component 10 was sieve through a screen with a mesh size of 0.3-0.4 mm, it was incorporated into the homogeneous mixture obtained in section "e", and the whole was mixed in a suitable container for approximately 5 minutes;
g) the mixture powder obtained in stage "f" was compressed in a tabletting machine equipped with suitable punches.

| | |
| --- | --- |
| Disintegration time | 9 sec. |
| Weight | 75 mg |
| Resistance to crushing | 34 N |
| Friability | 0.20% |
| Thickness | 1.65 mm |

Example 5

The tablet was prepared according to the procedure described below using the formulation having the ingredients shown in table V:

TABLE V

| | mg | % (w/w) |
| --- | --- | --- |
| 1. Ondansetron base | 4.00 mg | 10.00% |
| 2. Lactose monohydrate | 27.95 mg | 69.88% |
| 3. Hydroxypropylcellulose low-substituted | 1.60 mg | 4.00% |
| 4. Crospovidone | 1.20 mg | 3.00% |
| 5. Calcium silicate | 3.60 mg | 9.00% |
| 6. Aspartame | 0.53 mg | 1.33% |
| 7. Peppermint flavour | 0.52 mg | 1.30% |
| 8. Colloidal anhydrous silica | 0.20 mg | 0.50% |
| 9. Magnesium stearate | 0.40 mg | 1.00% |
| Total | 40 mg | 100% |

Manufacturing Method

The orodispersible table was obtained according to the following procedure:
a) the components of the formulation were weighted;
b) components 4 and 5 were sieved through a screen with a mesh size of 0.5-0.6 mm;
c) the materials of stage "b" were mixed in a suitable container until a homogeneous mixture was obtained;
d) components 1, 2, 3, 6, 7 and 8 were sieved through a screen with a mesh size of 0.5-0.6 mm;

e) the materials of stage "d" were mixed with the blend obtained in stage "c" in a suitable container until a homogeneous mixture was obtained;
f) the component 9 was sieved through a screen with a mesh size of 0.3-0.4 mm, it was incorporated into the homogeneous mixture obtained in section "e", and the whole was mixed in a suitable container for approximately 5 minutes;
g) the mixture powder obtained in stage "f" was compressed in a tabletting machine equipped with suitable punches.

| | |
|---|---|
| Disintegration time | 6 sec. |
| Weight | 40 mg |
| Resistance to crushing | 21 N |
| Friability | 0.34% |
| Thickness | 1.02 mm |

Example 6

The tablet was prepared according to the procedure described below using the formulation having the ingredients shown in table VI:

TABLE VI

| | mg | % (w/w) |
|---|---|---|
| 1. Risperidone | 2.00 mg | 2.50% |
| 2. Lactose monohydrate | 64.3 mg | 80.40% |
| 3. Crospovidone | 2.50 mg | 3.10% |
| 4. Calcium silicate | 7.50 mg | 9.40% |
| 5. Sodium Cyclamate | 2.00 mg | 2.50% |
| 6. Cherry Flavor | 0.40 mg | 0.50% |
| 7. Colloidal anhydrous silica | 0.40 mg | 0.50% |
| 8. Magnesium stearate | 0.90 mg | 1.10% |
| Total | 80 mg | 100% |

Manufacturing Method
a) the components of the formulation were weighted;
b) components 3 and 4 were sieved through a screen with a mesh size of 0.5-0.6 mm;
c) the materials of stage "b" were mixed in a suitable container until a homogeneous mixture was obtained;
d) components 1, 2, 5, 6 and 7 were sieved through a screen with a mesh size of 0.5-0.6 mm;
e) the materials of stage "d" were mixed with the blend obtained in stage "c" in a suitable container until a homogeneous mixture was obtained;
f) the component 8 was sieved through a screen with a mesh size of 0.3-0.4 mm, it was incorporated into the homogeneous mixture obtained in section "e", and the whole was mixed in a suitable container for approximately 5 minutes
g) the mixture powder obtained in stage "f" was compressed in a tabletting machine equipped with suitable punches.

| | |
|---|---|
| Disintegration time | 12 sec. |
| Weight | 80 mg |
| Resistance to crushing | 37 N |
| Friability | <0.1% |
| Thickness | 1.80 mm |

The invention claimed is:

1. An orally disintegrating tablet obtained by direct compression of a dry powdered mixture, said mixture comprising:
    up to 15% by weight of calcium silicate;
    at least 50% by weight of lactose;
    at least one disintegrant; and
    olanzapine,
wherein said orally disintegrating tablet presents a friability no greater than 1% and a disintegration time of less than 20 seconds, and wherein the dry powder mixture has not been subjected to any granulation process, dissolution, or dispersion in a liquid medium.

2. The tablet according to claim 1, wherein the tablet's thickness is less than 30% of the tablet's major diameter.

3. The tablet according to claim 1, wherein the calcium silicate is crystalline.

4. The tablet according to claim 1, wherein the calcium silicate is ortho-, meta- or alpha triclinic-calcium silicate.

5. The tablet according to claim 1, wherein said calcium silicate is amorphous.

6. The tablet according to claim 1, wherein the lactose is lactose, anhydrous lactose, lactose monohydrate, agglomerated lactose or atomised forms of lactose.

7. The tablet according to claim 1, wherein the disintegrant is selected from the group consisting of crospovidone, sodium croscarmellose, sodium starch glycolate, low-substituted hydroxypropyl cellulose and pregelatinized starch.

8. The tablet according to claim 7, wherein the disintegrant is crospovidone or sodium croscarmellose.

9. The tablet according to claim 1, wherein the powdered mixture further comprises an effervescent component.

10. The tablet according to claim 1, wherein the dry powder comprises from 1 to 20% by weight of olanzapine.

11. The tablet according to claim 1, wherein said calcium silicate, lactose, at least one disintegrant, and olanzapine have been previously and independently passed through a sieve with mesh size lower than 650 μm.

12. A process for the preparation of a tablet as defined in claim 1, said process comprising:
    i. mixing the dry powdered ingredients in the required amount, and
    ii. applying direct compression to the mixture obtained in step i),
wherein the mixture obtained in step i) has not been subjected to any granulation process, dissolution, or dispersion in a liquid medium.

13. The tablet according to claim 1, wherein the mixture comprises up to 10 weight % of calcium silicate.

14. The process of claim 12, wherein said calcium silicate, lactose, at least one disintegrant, and olanzapine have been previously and independently passed through a sieve with mesh size lower than 650 μm.

* * * * *